United States Patent [19]

Morris

[11] Patent Number: 5,374,286

[45] Date of Patent: Dec. 20, 1994

[54] TORQUE INDICATOR FOR FIXED SCREW LEADS

[75] Inventor: Mary M. Morris, Mounds View, Minn.

[73] Assignee: Medtronic, Inc., Minneapolis, Minn.

[21] Appl. No.: 40,735

[22] Filed: Mar. 31, 1993

[51] Int. Cl.$^5$ .............................................. A61N 1/02
[52] U.S. Cl. .................................. 607/119; 128/642; 607/127
[58] Field of Search ............... 128/642; 607/116, 119, 607/122, 123, 126, 127, 128; 604/282

[56] References Cited

U.S. PATENT DOCUMENTS

| | | |
|---|---|---|
| 3,974,834 | 8/1976 | Kane . |
| 4,046,151 | 9/1977 | Rose . |
| 4,106,512 | 8/1978 | Bisping ................................ 607/127 |
| 4,146,036 | 3/1979 | Dutcher et al. . |
| 4,217,913 | 8/1980 | Dutcher ................................ 607/127 |
| 4,282,885 | 8/1981 | Bisping ................................ 607/127 |
| 4,447,239 | 5/1984 | Krütten ................................ 604/282 |
| 4,570,642 | 2/1986 | Kane et al. . |
| 4,572,605 | 2/1986 | Hess ...................................... 339/177 |
| 4,771,777 | 9/1988 | Horzewski et al. . |
| 4,953,564 | 9/1990 | Berthelson .................. 607/127 X |
| 5,279,299 | 1/1994 | Imran ................................ 607/130 X |

FOREIGN PATENT DOCUMENTS 2504394 10/1982 France ................................ 128/642

OTHER PUBLICATIONS

*Fundamentals of Radiology*, 1964, pp. 1–13.

Primary Examiner—William E. Kamm
Assistant Examiner—Jeffrey R. Jastrzab
Attorney, Agent, or Firm—Harold R. Patton; Dianne M. Plunkett

[57] ABSTRACT

A body-implantable lead (10) for use in cardiac pacing having a proximal end and a distal end, the proximal end connected to a medical device, an active fixation device such as a helix electrode (330) having a distal end and a proximal end, the tissue securing means extending from the lead body distal end, an electrical conductor (15) extending between the proximal and distal ends of the lead, and a longitudinally extending radiopaque marker (35 or 335) affixed to the lead body (10) proximal to the tissue securing means, the radiopaque marker (35 or 335) showing rotational movement or distortion of the radiopaque marker (35 or 335) under fluoroscopy.

20 Claims, 3 Drawing Sheets

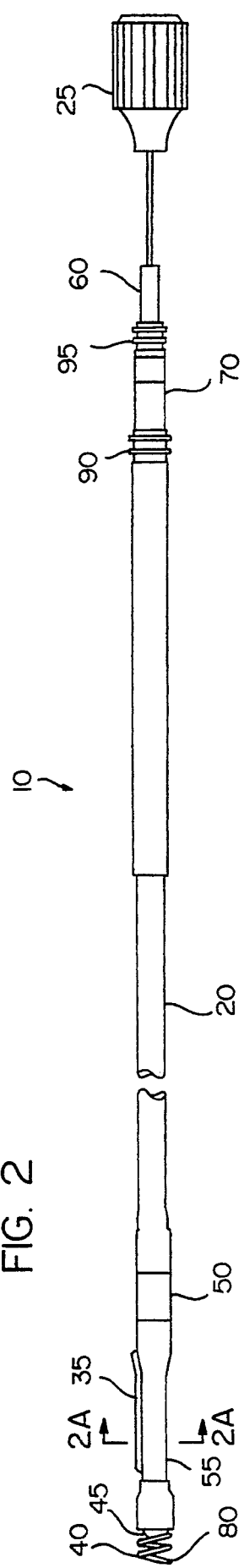
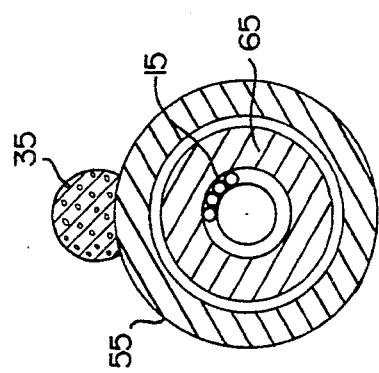
FIG. 2
FIG. 2A

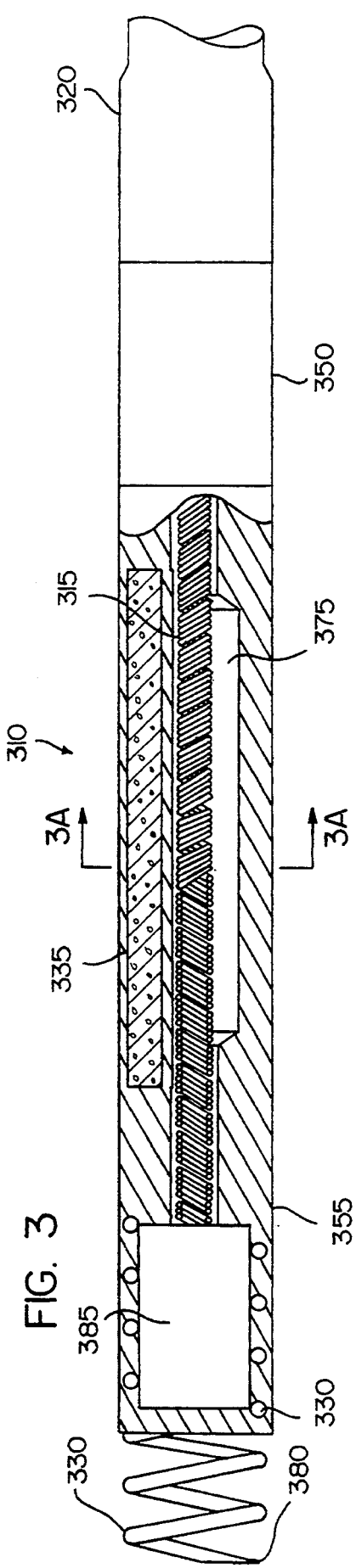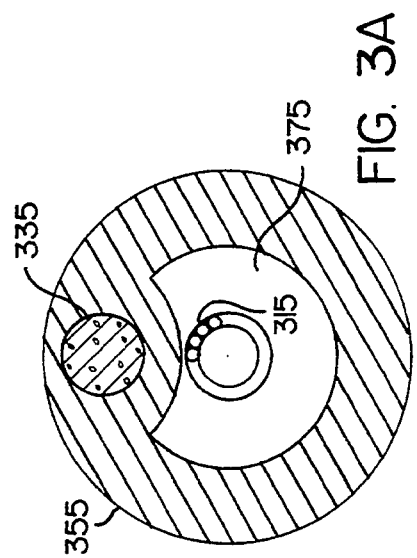

TORQUE INDICATOR FOR FIXED SCREW LEADS

FIELD OF THE INVENTION

The present invention relates to a lead bearing an electrode for electrically connecting an organ inside a living animal body to an electrical device and more particularly to cardiac pacing leads.

BACKGROUND OF THE INVENTION

There are generally two types of body-implantable leads used with cardiac pacemakers, myocardial and endocardial. Myocardial leads presently require surgery to expose the myocardial tissue to which the electrode is affixed.

Endocardial leads have an electrode or electrodes located at the distal end, are inserted in and guided through a body vessel such as a vein into the heart where the electrodes contact, and in some cases, are secured to the heart through the endothelial tissue lining the heart interior. Endocardial leads are divided into active and passive fixation leads. Passive fixation leads are nonpenetrating leads. Tines are an example of passive fixation leads. Active fixation leads are penetrating leads. Applicant's fixed screw lead is an example of an active fixation lead.

An important feature of an endocardial lead is that of having a means of securing the electrode to the heart without dislodgment. Active fixation leads reduce dislodgments. A disadvantage of prior art leads is that it is difficult to know when the lead has been successfully embedded in the cardiac tissue. With a fixed screw lead it is difficult to judge how many turns are necessary to embed or remove the helix without turning the lead too many times thereby causing undue trauma to the tissue. With such leads, the physician must tactually determine the number of rotations necessary to achieve lead fixation.

Endocardial screw-in type leads are well known in the art as for example, U.S. Pat. No. 4,146,036 to Dutcher et al which discloses a unipolar fixed screw lead. With such leads, the physician tactually determines the number of rotations necessary to achieve lead fixation.

U.S. Pat. No. 4,570,642 to Kane et al discloses an endocardial, unipolar, extendable screw-in lead. With such leads, the physician observes helix extension under fluoroscopy during lead fixation.

U.S. Pat. No. 3,974,834 to Kane et al discloses an endocardial, bipolar, screw-in lead. With such leads, the physician tactually determines the number of rotations necessary to achieve lead fixation.

U.S. Pat. No. 4,046,151 to Rose discloses an endocardial, bipolar, screw-in lead. With such leads, the physician tactually determines the number of rotations necessary to achieve lead fixation.

U.S. Pat. No. 4,572,605 to Hess, discloses a typical connector assembly for a bipolar coaxial lead. With such leads, the physician tactually determines the number of rotations necessary to achieve lead fixation.

The use of fluoroscopy to detect longitudinal motion is well known in catheter art. See, U.S. Pat. No. 4,771,777 to Horzewski et al. at col. 4, lns. 17-20.

SUMMARY OF THE INVENTION

The present invention aids physicians in determining the amount of torque to apply when implanting or explanting leads. The number of rotations applied at the proximal end of the lead is not always equal to the number of rotations transferred to the distal end of the lead. The present invention provides a radiopaque marker on or near the outer diameter of the TR (Tip-to-Ring) spacer. The radiopaque marker may be external to the lead body or internal to the lead body. It is useful in two aspects. First, during implant, rotations of the radiopaque torque indicator strip are easier to count than the rotations of a symmetrical radiopaque helix. Second, after the helix is imbedded in the heart tissue the torque indicator initially appears co-linear; further rotation then causes distortion of the radiopaque torque indicator strip into a spiral configuration. Distortion of the torque indicator is visible under fluoroscopy as the torque indicator no longer is co-linear to the conductor spring coil and will be visible from all views.

The above features and advantages of the present invention, as well as others, are accomplished by providing a body-implantable lead having a proximal end and a distal end, the proximal end connected to a medical device, a tissue securing means having a distal end and a proximal end, the tissue securing means extending from the lead body distal end, an electrical conductor extending between the proximal and distal ends of the lead, and a longitudinally extending radiopaque marker affixed to the lead body proximal to the tissue securing means, the radiopaque marker showing rotational movement or distortion of the radiopaque marker under fluoroscopy. The tissue securing means comprises a helix axially aligned with the lead body and is attached to the electrical conductor. The helix may also be electrically insulated from the electrical conductor with the lead body having an electrode electrically connected to the distal end of the conductor. The radiopaque marker comprises a linear member and consists of a flexible radiopaque material of a cylindrical shape approximately 0.025 inches (0.0635 cm) in diameter and approximately 0.75 inches (1.9 cm) in length.

Other features, advantages and objects of the present invention will hereinafter become more fully apparent from the following description of the drawings, which illustrate the invention.

BRIEF DESCRIPTION OF THE DRAWINGS

FIG. 2 shows a view of a body-implantable, endocardial fixed screw lead with an electrically inactive helix, a separate electrically active electrode and an external torque indicator;

FIG. 2a shows a view of the cross-section of FIG. 2 along the lines 2—2;

FIG. 3 shows a view of an internal torque indicator inside elevation partly in longitudinal section which is an alternative embodiment of the distal end portion of the lead of FIG. 2; and FIG. 3a shows a view of the cross-section of FIG. 3 along the lines 3—3.

DETAILED DESCRIPTION OF THE PREFERRED EMBODIMENTS

Figure 1:
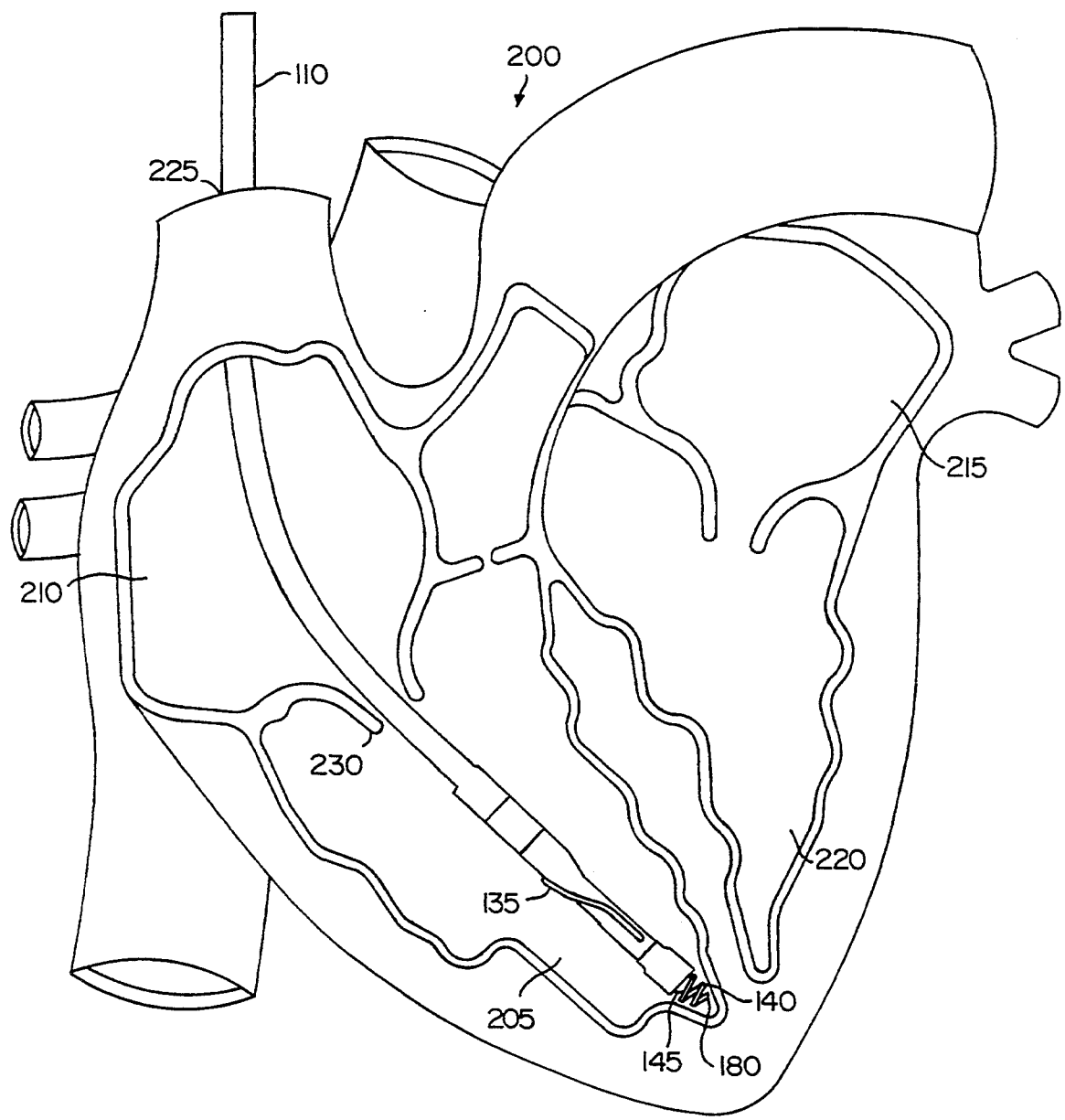
FIG. 1 shows the lead of FIG. 2 being lodged in and permanently secured to the tissue forming the apex of the right ventricle of the heart.

The following specification will first briefly describe the procedure for implanting a lead then describe the major lead components. These components are the electrode, spring coil conductor, torque indicator and its typical methods of manufacturing, tissue securing means such as the helix, outer tubing, tip to ring spacer, anode ring and sealing rings. For purposes of this application, the invention will be described for use as an endocardial pacing and sensing lead for connecting an artificial cardiac pacemaker to cardiac tissue. Nevertheless, the lead could as well be applied to other types of body stimulating systems. Although applicant's invention represents an endocardial type lead, the invention may apply to myocardial leads in the future, as for example with endoscopic equipment.

Referring to FIG. 1, the heart 200 in cross section comprises the four chambers, namely, the right ventricle 205, the right atrium 210, the left atrium 215 and the left ventricle 220. In the placement of an endocardial lead 110, it is preferable to use a venous approach on the low pressure side of the heart. For example, the typical ventricular path as depicted in FIG. 1, would begin through a vein such as the right or left external subclavian vein, or the right or left cephalic veins, then through the superior vena cava 225, the right atrium 210, the tricuspid valve 230 and to the right ventricle 205. Most screw-in leads are implanted in the right atrium. The stylet 25 as in FIG. 2 is used to control the location of implant.

After the lead 110 in FIG. 1 is passed through the tricuspid valve 230 and into the right ventricle 205, a suitable location for implant may be determined by placing the electrode 145 tip adjacent to the heart tissue and taking stimulation and/or sensing thresholds. After a suitable location has been determined, the lead 110 is rotated around stylet 25 as in FIG. 2 to screw helix 140 into the tissue at the desired stimulation site. The torque indicator 135 aids the physician in determining the proper number of rotations. After the helix 140 has been firmly affixed to the tissue, the stylet 25 is pulled proximally and removed from the lead 110.

The present invention can use either a unipolar or a bipolar lead; FIGS. 1–3 represent bipolar leads. A bipolar configuration carries two electrodes and two conductors. In FIG. 2 which depicts a lead with an external torque indicator 35, the two electrodes are shown as the anode ring 50 and the electrode 45. FIG. 3 depicts an alternative embodiment of FIG. 2, with FIG. 3 having an internal torque indicator 335. In FIG. 3, the two electrodes are shown as the anode ring 350 and the helix electrode 330. In both the FIG. 2 and FIG. 3 embodiments the two conductors comprise an outer spring coil and an inner spring coil. As for example, in FIG. 3, the outer spring coil is wound about and along the axis of the inner spring coil 315. The Tip-to-Ring (TR) Spacer 355 provides the electrically insulated separation between the two electrodes to permit signal sensing.

In a bipolar lead the two conductors may be co-axial or biaxial coils. In the illustrated embodiments, the coils are co-axial. The conductor spring coil construction is the same in both the external radiopaque marker 35 embodiment seen in FIG. 2 as in the internal radiopaque marker 335 embodiment seen in FIG. 3. The inner and outer conductors are both spring coils and can be formed of a nickel alloy. The inner spring coil 315 distal end is connected to the helix electrode 330 as in FIG. 3 and to the electrode 45 in FIG. 2 by a variety of means, as for example, through the use of a platinum alloy crimp tube. At the proximal end of both embodiments the inner spring coil is connected to the pin 60. The outer spring coil distal end is connected to the anode ring 50. At the proximal end the outer spring coil is connected to the connector ring 70. The inner spring coil in both embodiments extends through the length of the lead body in a tubular insulating sheath 65 extending between the inner spring coil 15 and outer spring coil, the sheath 65 comprising a lumen as seen in FIG. 2A. The outer spring coil extends through the length of the lead 10 in a lumen of outer tubing 20 of electrically insulating material. Both inner spring coil 15 and 315 as well as outer spring coil are formed of electrically conductive material offering low electrical resistance and resistance to corrosion by body fluids. A nickel alloy, such as MP35N, is an example of a suitable conductor material.

A lead such as 10 using a conductor coil such as inner spring coil 15 has been shown to be capable of withstanding constant, rapidly repeated flexing over a period of time which can be measured in years. The inner spring coil 15 is wound relatively tightly, although there can be a slight space between adjacent turns. The spirally coiled spring construction of the spring coil 15 also permits a substantial degree of elongation, within the elastic limits of the material, as well as distribution of flexing stresses along the conductor which otherwise might be concentrated at a particular point. Both the inner spring coil 15 and the outer tubing 20 are elastic, and this, together with the coiled construction of the inner spring coil 15, assures maximum distribution of flexing stresses. The spring coil 15 may also comprise a multi-filar redundant coil of thinner wire.

There are three methods for manufacturing a radiopaque marker for a torque indicator. The most preferable method as seen in FIG. 3 consists of a two step molding process. The first step molds the platinum loaded silicone torque indicator into a cylindrical shape. The torque indicator is removed from the mold after it cures. The second step places the pre-molded indicator into a TR spacer mold in a linear direction preferably near the outside diameter at a uniform depth and encases the torque indicator with silicone. A central cavity 375 in the TR Spacer mold will form a lumen through which the inner spring coil 315 will extend. The cavity is preferably not symmetrical as a thickened silicone area should be formed under the torque indicator 335 for strengthening. The cavity 375 contributes to the flexibility of the distal end of the lead body 310. The greater the cavity 375, the greater the flexibility.

The second method of manufacturing torque indicators includes backfilling a lumen with platinum loaded adhesive as seen in FIG. 3. Mold a second lumen in the TR spacer 355 in addition to the lumen for the conductor coil. Fill the second lumen which is near the outside diameter of the TR spacer 355 with uncured platinum loaded adhesive.

The third method of manufacturing a torque indicator, which can be seen in FIG. 2, includes applying an uncured platinum loaded adhesive directly to the outside of the TR spacer 55. The adhesive bonds to the exterior of the TR spacer.

Those skilled in the art will recognize that there are other methods of manufacturing a radiopaque marker. Radiopaque foils, radiopaque coils or silicone elastomer with platinum milled in could be used.

The torque indicator 35 or 335 can be made of biocompatible radiopaque materials such as platinum, iridium, gold or tantalum. It is more preferably made of platinum loaded silicone with a concentration of 4 grams per cc of silicone adhesive. The optional concentration of the radiopaque element is a function of the torque indicator's thickness and type of radiopaque material selected. The preferred torque indicator diameter is approximately 0.025 inches (0.0635 cm) with a length of approximately 0.75 inches (1.9 cm).

The tissue securing means and electrode could be combined as a unitary entity or could be separate entities. An example of a unitary entity is a fixed screw lead with the screw as the electrically active electrode 330 as in FIG. 3. An example of separate entities is a tissue securing means consisting of an electrically inactive fixed helix 40 and a separate electrically active electrode 45 as in FIGS. 1 and 2.

The tissue securing means can take the form of a relatively rigid circular corkscrew which can be either an electrically inactive helix 40 as in FIG. 2 or helix electrode 330 as shown in FIG. 3. This form of a helix consists of approximately two closely wound turns of platinum-iridium coil made of approximately 0.012 inch (0.0305 cm) diameter wire. These turns end in a sharpened tip 80 or 380 at a point on the inside circumference on the wire making it up. The tip readily penetrates the endocardium. The tip further penetrates the tissue with the addition of clockwise rotation of the proximal lead body. The tip extends beyond the distal end of the lead body by about 0.08 inches (0.20 cm).

When the helix 140 and 40 is electrically inactive as in FIG. 1 and 2 respectively, the distal end of the lead additionally has an electrode 145 or 45, electrically and mechanically coupled to an inner spring coil by a platinum alloy crimp tube. A flexible, insulating sheath 65 surrounds the inner spring coil and crimp tube. A suitable material for the insulating sheath 65 is silicone rubber. When the helix 40 is electrically inactive, it serves only as a means of securing and maintaining the electrode in firm engagement with the endocardial tissue. The helix then forms no part of the electrode structure. The helix 140 or 40 can be affixed as follows. The helix may be molded in place with silicone elastomer. A crimp or laser weld is provided at the distal end to attach the electrode to the inner spring coil.

To create an electrically active helix electrode 330 as in FIG. 3, the crimp or laser weld would connect the helix electrode 330 to the inner spring coil 315. The electrically inactive helix 40 and helix electrode 330 can both be made of a biocompatible metal, such as platinum, MP35N alloy, or elgiloy.

Outer tubing 20 or 320 is formed of an electrically insulating material, and preferably a silicone rubber, such as clean room grade Silastic available from Dow Corning Corporation or a polyether urethane, such as Pellethane ® CPR ® 2363-80AE available from the Upjohn Company. These materials are additionally suitable because they are inert and well tolerated by body tissue. In any of the disclosed embodiments the distal end of the lead body should be more flexible than the proximal end of the lead body to prevent undue stress on the myocardium. This region will generally be more flexible because only the inner spring coil 15 or 315 is present, the outer spring coil having ended at the anode ring 50 or 350. Further flexibility can be accomplished by either decreasing the thickness of the TR spacer 55 or 355 wall or using more flexible material at the distal end of the outer tubing 20 or 320 than at the proximal end of the outer tubing. Furthermore, in the FIG. 3 internal torque indicator embodiment, the size of cavity 375 can be adjusted. The greater the cavity 375, the greater the flexibility.

The TR (Tip to Ring) spacer 55 lies between the anode ring 50 and the helix 40 in FIG. 2 or between the anode ring 350 and the helix electrode 330 in FIG. 3. It is made of insulating material such as silicone. It electrically insulates the inner spring coil 15 or 315 from the tissue.

The anode ring 50 or 350 is electrically active and completes the electrical circuit. It is typically formed of a polished platinum alloy with an exposed surface area much larger than that of the electrode 45 in FIG. 2 or helix electrode 330 in FIG. 3.

Sealing rings 95 and 90 as in FIG. 2 both serve to prevent entry of body fluids into the lead assembly and prevent electrically shorting by a conductive fluid. They also mechanically stabilize the lead within the pacemaker connector block. The proximal end of the lead body is the same for both the FIG. 2 external torque indicator embodiment as for the FIG. 3 internal torque indicator embodiment. Sealing rings can be affixed with a variety of methods, one of which follows. The first sealing ring 95 lies over the top of a crimp tube to which the inner spring coil 15 or 315 is connected. The inner spring coil is also connected to the pin 60. The first sealing ring 95 prevents shorting by a conductive fluid path from the pin 60 to the connector ring 70. The second sealing ring 90 lies over the top of a crimp tube to which the outer spring coil is connected. The second sealing ring prevents shorting by preventing a fluid path between the body tissue and the connector ring 70.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|-----|-----------|
| 10 | Lead |
| 15 | Inner Spring Coil |
| 20 | Outer Tubing |
| 25 | Stylet |
| 35 | External Torque Indicator |
| 40 | Electrically Inactive Helix |
| 45 | Electrode |
| 50 | Anode Ring |
| 55 | TR Spacer |
| 60 | Pin |
| 65 | Insulating Sheath |
| 70 | Connector Ring |
| 80 | Tip |
| 90 | Second Sealing Ring |
| 95 | First Sealing Ring |
| 110 | Lead |
| 135 | External Torque Indicator |
| 140 | Electrically Inactive Helix |
| 145 | Electrode |
| 180 | Tip |
| 200 | Heart |
| 205 | Right Ventricle |
| 210 | Right Atrium |
| 215 | Left Atrium |
| 220 | Left Ventricle |
| 230 | Tricuspid Valve |
| 310 | Lead |
| 315 | Inner Spring Coil |
| 320 | Outer Tubing |
| 330 | Helix Electrode |
| 335 | Internal Torque Indicator |
| 350 | Anode Ring |
| 355 | TR Spacer |
| 375 | Cavity |
| 380 | Tip |
| 385 | Crimp Tube |

What is claimed is:

1. A body-implantable lead comprising:
   a lead body having a center axis, a proximal end and a distal end;
   means for securing said distal end of said lead body to tissue, said means for securing extending from said lead body distal end;
   an electrical conductor extending between said proximal and distal ends of said lead body; and
   a radiopaque marker having a center axis, said radiopaque marker affixed to said lead body at a position so that said radiopaque marker center axis is offset from said lead body center axis wherein said lead body has a first section and a second section, said first section has greater flexibility than said second section, and said radiopaque marker is affixed to said first section of said lead body.

2. A lead according to claim 1 wherein said radiopaque marker is affixed to said lead body proximal to said means for securing said distal end of said lead body to tissue.

3. A lead according to claim 1 wherein said means for securing said distal end of said lead body to tissue comprises a helix axially aligned with said lead body.

4. A lead according to claim 3 wherein said helix is connected to said electrical conductor.

5. A lead according to claim 3 further comprising said helix is at least partially insulated.

6. A lead according to claim 5 having an electrode electrically connected to said conductor at said distal end of said lead body.

7. A lead according to claim 1 wherein said radiopaque marker center axis is parallel to said lead body center axis.

8. A lead according to claim 1 wherein said first section has a cavity.

9. A lead according to claim 8 wherein said radiopaque marker comprises a linear member.

10. A lead according to claim 9 wherein said radiopaque marker is flexible.

11. A lead according to claim 9 wherein said radiopaque marker has a linear cylindrical shape.

12. A lead according to claim 1 wherein said radiopaque marker is affixed internally to said lead body.

13. A lead according to claim 12 wherein said conductor and said radiopaque marker are separated by a cavity.

14. A lead according to claim 1 wherein said radiopaque marker is affixed externally to said lead body.

15. A body-implantable lead comprising:
    a lead body having an outer wall, a proximal end and a distal end;
    an electrical conductor extending between said proximal and distal ends of said lead body;
    a helix attached to said distal end of said lead body, said helix axially aligned with said lead body; and
    a radiopaque marker affixed to said outer wall of said lead body proximal to said helix Wherein said lead body has a first section and a second section, said first section being located near said distal end, said second section being located near said proximal end, said first section be in a more flexible than said second section.

16. A body-implantable lead according to claim 15 wherein said helix is electrically attached to said conductor.

17. A body-implantable lead according to claim 15 further comprising an electrode positioned at said distal end of said lead body said electrode connected to said conductor.

18. A body-implantable lead according to claim 15 wherein said first section has a non-symmetrical cavity.

19. A body-implantable lead according to claim 15 wherein said first section has a cavity.

20. (New) A body-implantable lead according to claim 15 wherein said radiopaque marker is integral with said lead body.

* * * * *